United States Patent [19]
Krenzer

[11] 3,944,409
[45] Mar. 16, 1976

[54] METHOD OF INCREASING THE YIELD OF PLANTS HAVING STORAGE ORGANS BY TREATMENT WITH THIADIAZOLYLIMIDAZOLINES

[75] Inventor: John Krenzer, Oak Park, Ill.
[73] Assignee: Velsicol Chemical Corporation, Chicago, Ill.
[22] Filed: Dec. 19, 1974
[21] Appl. No.: 531,128

[52] U.S. Cl............................... 71/90; 260/306.8 D
[51] Int. Cl.².............................................. A01N 9/22
[58] Field of Search......................................... 71/90

[56] References Cited
UNITED STATES PATENTS

| | | | |
|---|---|---|---|
| 3,759,939 | 9/1973 | Metzger et al........................... | 71/90 |
| 3,773,780 | 11/1973 | Metzger et al........................... | 71/90 |
| 3,849,432 | 11/1974 | Metzger et al........................... | 71/90 |

Primary Examiner—Lewis Gotts
Assistant Examiner—Catherine L. Mills
Attorney, Agent, or Firm—Robert J. Schwarz; Dietmar H. Olesch

[57] ABSTRACT

This invention discloses a method of increasing the yield of plant food contained in plant storage organs which comprises contacting the plants having storage organs with from about 0.05 to about 4.0 pounds per acre of a compound of the formula

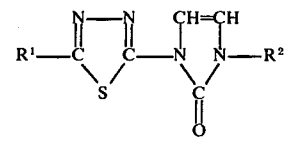

wherein $R^1$ is selected from the group consisting of alkyl, alkenyl, chloroalkyl, trifluoromethyl, alkoxy, alkylthio, alkylsulfonyl, alkylsulfinyl and cycloalkyl of from 3 to 7 carbon atoms optionally substituted with from 1 to 2 substituents selected from the group consisting of alkyl, alkoxy and halogen; and $R^2$ is alkyl.

7 Claims, No Drawings

METHOD OF INCREASING THE YIELD OF PLANTS HAVING STORAGE ORGANS BY TREATMENT WITH THIADIAZOLYLIMIDAZOLINES

This invention relates to a method of treating plants with storage organs thereby increasing the yield of plant food contained in the storage organs.

A variety of chemicals have been investigated as plant growth stimulants and promoters in attempts to increase the yield obtained from cultivated crops. These investigations have met with varying success but have not led to compositions of any commercial significance. In many instances the benefit derived from such compositions is offset by damage to the plant, such a disfuguration.

It has now been found that certain thiadiazolylimidazolines have the ability of increasing the yield of plant food contained in plant storage organs without exhibiting substantial toxicity to the plants. More specifically the present invention resides in a method of increasing the yield of plant food contained in plant storage organs which comprises contacting plants having storage organs with from about 0.05 pound to about 4.0 pounds per acre of a compound of the formula

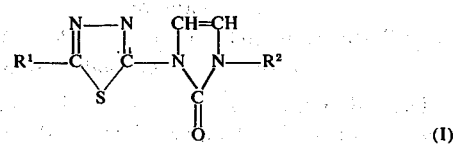

(I)

wherein $R^1$ is selected from the group consisting of alkyl, alkenyl, chloroalkyl, trifluoromethyl, alkoxy, alkylthio, alkylsulfonyl, alkylsulfinyl and cycloalkyl of from 3 to 7 carbon atoms optionally substituted with from 1 to 2 substituents selected from the group consisting of alkyl, alkoxy and halogen; and $R^2$ is alkyl.

In a preferred embodiment of this invention $R^1$ is selected from the group consisting of lower alkyl, lower alkenyl lower chloroalkyl, trifluoromethyl, lower alkoxy, lower alkylthio, lower alkylsulfonyl, lower alkylsulfinyl and cycloalkyl of from 3 to 7 carbon atoms optionally substituted with from 1 to 2 substituents selected from the group consisting of lower alkyl, lower alkoxy, chlorine, bromine and fluorine; and $R^2$ is lower alkyl.

The term lower as used herein designates a straight or branched carbon chain of up to six carbon atoms.

The compounds of this invention can be prepared by dehydrating a compound of the formula

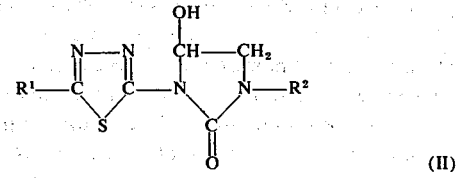

(II)

wherein $R^1$ and $R^2$ are as heretofore defined. This dehydration can be effected by reacting the compound of formula II with an about equimolar or slight excess molar amount of thionyl chloride. This reaction can be carried out by adding the thionyl chloride to a solution of the compound of formula II in an inert organic solvent such as methylene chloride at a temperature of from about 0°C to about 20°C. After the addition is completed the reaction mixture can be allowed to stand at room temperature for a period of from about 1 to about 24 hours to ensure completion of the reaction. After this time the reaction mixture can be stripped of solvent under reduced pressure to yield the desired product as the residue. This product can then be used as such or can be further purified by conventional techniques such as recrystallization and the like.

The compounds of formula II can be readily prepared by heating a compound of the formula

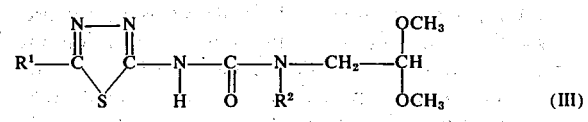

(III)

wherein $R^1$ and $R^2$ are as heretofore described, in a dilute, aqueous, acidic reaction medium for a period of about 10 to about 60 minutes. Temperatures of from about 70°C to the reflux temperature of the reaction mixture can be utilized. The reaction medium can comprise a dilute aqueous inorganic acid such as hydrochloric acid at a concentration of from about 0.5 to about 5 percent. Upon completion of the reaction the desired product can be recovered as a precipitate by cooling the reaction mixture. This product can be used as such or can be further purified by conventional means such as recrystallization and the like.

The compounds of formula III can be prepared by reacting a molar amount of an isocyanate dimer of the formula

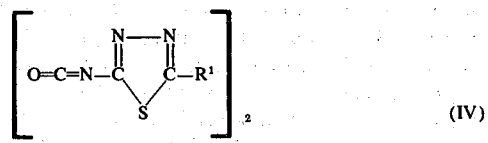

(IV)

wherein $R^1$ is as heretofore described, with about two molar amounts of a dimethyl acetal of the formula

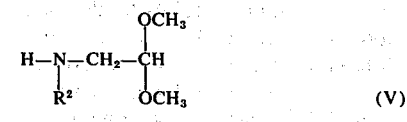

(V)

wherein $R^2$ is as heretofore described. This reaction can be effected by heating a mixture of the isocyanate dimer and the acetal in an inert organic reaction medium such as benzene at the reflux temperature of the reaction mixture. Heating at reflux can be continued for a period of from about 2 to about 30 minutes to ensure completion of the reaction. After this time the desired product can be recovered upon evaporation of the reaction medium and can be used as such or can be further purified by standard techniques in the art.

The isocyanate dimer of formula IV can be prepared by reacting a thiadiazole of the formula

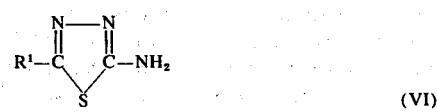

(VI)

wherein $R^1$ is as heretofore described, with phosgene. This reaction can be effected by adding a slurry or solution of the thiadiazole, in a suitable organic solvent such as ethyl acetate, to a saturated solution of phosgene in an organic solvent such as ethyl acetate. The resulting mixture can be stirred at ambient temperatures for a period of from about 4 to about 24 hours. The reaction mixture can then be purged with nitrogen gas to remove unreacted phosgene. The desired product can then be recovered by filtration if formed as a precipitate or upon evaporation of the organic solvent used if soluble therein. This product can be used as such or can be further purified if desired.

Exemplary thiadiazoles of formula VI useful for preparing the compounds of the present invention are 5-methyl-2-amino-1,3,4-thiadiazole, 5-ethyl-2-amino-1,3,4-thiadiazole, 5-propyl-2-amino-1,3,4-thiadiazole, 5-allyl-2-amino-1,3,4-thiadiazole, 5-pent-3-enyl-2-amino-1,3,4-thiadiazole, 5-chloromethyl-2-amino-1,3,4-thiadiazole, 5-β-chloroethyl-2-amino-1,3,4-thiadiazole, 5-γ-chloropropyl-2-amino-1,3,4-thiadiazole, 5-trichloromethyl-2-amino-1,3,4-thiadiazole, 5-methoxy-2-amino-1,3,4-thiadiazole, 5-ethoxy-2-amino-1,3,4-thiadiazole, 5-propoxy-2-amino-1,3,4-thiadiazole, 5-butyloxy-2-amino-1,3,4-thiadiazole, 5-hexyloxy-2-amino-1,3,4-thiadiazole, 5-methylthio-2-amino-1,3,4-thiadiazole, 5-ethylthio-2-amino-1,3,4-thiadiazole, 5-propylthio-2-amino-1,3,4-thiadiazole, 5-butylthio-2-amino-1,3,4-thiadiazole, 5-methylsulfonyl-2-amino-1,3,4-thiadiazole, 5-ethylsulfonyl-2-amino-1,3,4-thiadiazole, 5-butylsulfonyl-2-amino-1,3,4-thiadiazole, 5-methylsulfinyl-2-amino-1,3,4-thiadiazole, 5-ethysulfinyl-2-amino-1,3,4-thiadiazole, 5-propylsulfinyl-2-amino-1,3,4-thiadiazole, 5-t-butyl-2-amino-1,3,4-thiadiazole, 5-trifluoromethyl-2-amino-1,3,4-thiadiazole, 5-cyclopropyl-2-amino-1,3,4-thiadiazole, 5-cyclobutyl-2-amino-1,3,4-thiadiazole, 5-cyclopentyl-2-amino-1,3,4-thiadiazole, 5-cyclohexyl-2-amino-1,3,4-thiadiazole, 5-cycloheptyl-2-amino-1,3,4-thiadiazole, 5-(2-methylcyclopropyl)-2-amino-1,3,4-thiadiazole, 5-(3-ethylcyclopentyl)-2-amino-1,3,4-thiadiazole, 5-(4-propylcyclohexyl)-2-amino-1,3,4-thiadiazole, 5-(1-methylcyclohexyl)-2-amino-1,3,4-thiadiazole, 5-(4-chlorocyclohexyl)-2-amino-1,3,4-thiadiazole, 5-(4-bromocyclohexyl)-2-amino-1,3,4-thiadiazole, 5-(4-fluorocyclohexyl)-2-amino-1,3,4-thiadiazole, 5-(3-methoxycyclohepty)-2-amino-1,3,4-thiadiazole, 5-(3-hexylcyclopentyl)-2-amino-1,3,4-thiadiazole, 5-(4-hexyloxycyclohexyl)-2-amino-1,3,4-thiadiazole, 5-(4-iodocyclohexyl)-2-amino-1,3,4-thiadiazole and the like.

The manner in which the compounds of this invention can be prepared is more specifically illustrated in the following examples.

EXAMPLE 1

Preparation of 5-Trifluoromethyl-1,3,4-thiadiazol-2-yl Isocyanate Dimer

A saturated solution of phosgene in ethyl acetate (100 ml) was charged into a glass reaction vessel equipped with a mechanical stirrer. A slurry of 5-trifluoromethyl-2-amino-1,3,4-thiadiazole (45 grams) in ethyl acetate (300 ml) was added to the reaction vessel and the resulting mixture was stirred for a period of about 16 hours resulting in the formation of a precipitate. The reaction mixture was then purged with nitrogen gas to remove unreacted phosgene. The purged mixture was filtered to recover 48 grams of a white solid. This solid was recrystallized from dimethyl formamide to yield the desired product 5-trifluoromethyl-1,3,4-thiadiazol-2-yl isocyanate dimer.

EXAMPLE 2

Preparation of the Dimethyl Acetal of 2-[1-Methyl-3-(5-trifluoromethyl-1,3,4-thiadiazol-2-yl)ureido]acetaldehyde A mixture of 5-trifluoromethyl-1,3,4-thiadiazol-2-yl isocyanate dimer (9.5 grams), the dimethyl acetal of 2-methylaminoacetaldehyde (5.8 grams) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. This product is recrystallized from heptane to yield the desired product the dimethyl acetal of 2-[1-methyl-3-(5-trifluoromethyl-1,3,4-thiadiazol-2-yl)ureido]acetaldehyde having a melting point of 101° to 102°C.

EXAMPLE 3

Preparation of 1-(5-Trifluoromethyl-1,3,4-thiadiazol-2-yl)-3-methyl-5-hydroxy-1,3-imidazolidin-2-one The dimethyl acetal of 2-[1-methyl-3-(5-trifluoromethyl-1,3,4-thiadiazol-2-yl)ureido]acetaldehyde (15 grams), water (400 ml) and hydrochloric acid (4 ml) were charged into a glass reaction vessel equipped with a mechanical stirrer, thermometer and reflux condenser. The reaction mixture was heated at reflux for a period of about 15 minutes. The reaction mixture was then filtered while hot and the filtrate was cooled resulting in the formation of a precipitate. The precipitate was recovered by filtration, was dried and was recrystallized from an ethyl acetatehexane mixture to yield the desired product 1-(5-trifluoromethyl-1,3,4-thiadiazol-2-yl)-3-methyl-5-hydroxy-1,3-imidazolidin-2-one having a melting point of 136° to 138°C.

EXAMPLE 4

Preparation of 1-(5-Trifluoromethyl-1,3,4-thiadiazol-2-yl)-3-methyl-1,3-imidazolin-2-one A solution of 1-(5-trifluoromethyl-1,3,4-thiadiazol-2-yl)-3-methyl-5-hydroxy-1,3-imidazolidin-2-one (7 grams) in methylene chloride (50 ml) was charged into a glass reaction vessel equipped with a mechanical stirrer and thermometer. The solution was cooled to a temperature of about 10°C and thionyl chloride (3 ml) was added with stirring. After the addition was completed the reaction mixture was allowed to stand at room temperature overnight. After this time the reaction mixture was stripped of methylene chloride by vacuum distillation leaving a solid residue. The residue was recrystallized from heptane to yield the desired product 1-(5-trifluoromethyl-1,3,4-thiadiazol-2-yl)-3-methyl-1,3-imidazolin-2-one having a melting point of 135° to 137°C.

EXAMPLE 5

Preparation of 5-t-Butyl-1,3,4-thiadiazol-2-yl Isocyanate Dimer

A saturated solution of phosgene in ethyl acetate (100 ml) was charged into a glass reaction vessel equipped with a mechanical stirrer. A slurry of 5-t-butyl-2-amino-1,3,4-thiadiazole (10 grams) in ethyl acetate (300 ml) was added to the reaction vessel and the resulting mixture was stirred for a period of about 16 hours resulting in the formation of a precipitate. The reaction mixture was then purged with nitrogen gas to remove unreacted phosgene. The purged mixture was then filtered to recover the desired product 5-t-butyl-1,3,4-thiadiazol-2-yl isocyanate dimer as a solid having a melting point of 261° to 263°C.

EXAMPLE 6

Preparation of the Dimethyl Acetal of 2-[1-methyl-3-(5-t-butyl-1,3,4-thiadiazol-2-yl)ureido]acetaldehyde A mixture of 5-t-butyl-1,3,4-thiadiazol-2-yl isocyanate dimer (6 grams), the dimethyl acetal of 2-methylaminoacetaldehyde (3.9 grams) and benzene (50 ml) was charged into a glass reaction flask equipped with a mechanical stirrer and reflux condenser. The reaction mixture was heated at reflux, with stirring for a period of about 5 minutes. After this time the reaction mixture was stripped of benzene to yield an oil which solidified upon standing. The resulting solid was then recrystallized from pentane to yield the desired product the dimethyl acetal of 2-[1-methyl-3-(5-t-butyl-1,3,4-thiadiazol-2-yl)ureido]acetaldehyde having a melting point of 80° to 82°C.

EXAMPLE 7

Preparation of 1-(5-t-Butyl-1,3,4-thiadiazol-2-yl)-3-methyl-5-hydroxy-1,3-imidazolidin-2-one The dimethyl acetal of 2-[1-methyl-3-(5-t-butyl-1,3,4-thiadiazol-2-yl)ureido]acetaldehyde (16 grams), concentrated hydrochloric acid (10 ml) and water (500 ml) were charged into a glass reaction vessel equipped with a mechanical stirrer, thermometer and reflux condenser. The reaction mixture was heated at reflux for a period of about 15 minutes. The reaction mixture was filtered while hot and the filtrate was then cooled, resulting in the formation of a precipitate. The precipitate was recovered by filtration, dried and was recrystallized from a benzene-hexane mixture to yield the desired product 1-(5-t-butyl-1,3,4-thiadiazol-2-yl)-3-methyl-5-hydroxy-1,3-imidazolidin-2-one having a melting point of 133° to 134°C.

EXAMPLE 8

Preparation of 1-(5-t-Butyl-1,3,4-thiadiazol-2-yl)-3-methyl-1,3-imidazolin-2-one A solution of 1-(5-t-butyl-1,3,4-thiadiazol-2-yl)-3-methyl-5-hydroxy-1,3-imidazolidin-2-one (7 grams) in methylene chloride (50 ml) was charged into a glass reaction vessel equipped with a mechanical stirrer and thermometer. The solution was cooled to a temperature of about 10°C and thionyl chloride (3 ml) was added with stirring. After the addition was completed the reaction mixture was allowed to stand at room temperature overnight. After this time the reaction mixture was stripped of methylene chloride by vacuum distillation having a solid residue. The residue was then recrystallized from hexane to yield the desired product 1-(5-t-butyl-1,3,4-thiadiazol-2-yl)-3-methyl-1,3-imidazolin-2-one having a melting point of 114° to 116°C.

EXAMPLE 9

Preparation of 5-Methyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-methyl-2-amino-1,3,4-thiadiazole (40 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methyl-1,3,4-thiadiazol-2-yl isocyanate dimer.

EXAMPLE 10

Preparation of the Dimethyl Acetal of 2-[1-Methyl-3-(5-methyl-1,3,4-thiadiazol-2-yl)ureido]acetaldehyde A mixture of 5-methyl-1,3,4-thiadiazol-2-yl isocyanate dimer (0.05 mole), the dimethyl acetal of 2-methylaminoacetaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product dimethyl acetal of 2-[1-methyl-3-(5-methyl-1,3,4-thiadiazol-2-yl)ureido]-acetaldehyde.

EXAMPLE 11

Preparation of 1-(5-Methyl-1,3,4-thiadiazol-2-yl)-3-methyl-5-hydroxy-1,3-imidazolidin-2-one The dimethyl acetal of 2-[1-methyl-3-(5-methyl-1,3,4-thiadiazol-2-yl)ureido]acetaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot and the filtrate is cooled to form a precipitate. The precipitate is recovered by filtration, is dried and is recrystallized to yield the desired product 1-(5-methyl-1,3,4-thiadiazol-2-yl)-3-methyl-5-hydroxy-1,3-imidazolidin-2-one.

EXAMPLE 12

Preparation of 1-(5-Methyl-1,3,4-thiadiazol-2-yl)-3-methyl-1,3-imidazolin-2-one A solution of 1-(5-methyl-1,3,4-thiadiazol-2-yl)-3-methyl-5-hydroxy-1,3-imidazolidin-2-one (7 grams) in methylene chloride (50 ml) is charged into a glass reaction vessel equipped with a mechanical stirrer and thermometer. The solution is cooled to a temperature of about 10°C and thionyl chloride (3 ml) is added with stirring. After the addition is completed the reaction mixture is allowed to stand at room temperature overnight. After this time the reaction mixture is stripped of methylene chloride by vacuum distillation leaving a solid residue. The residue is then recrystallized to yield the desired product 1-(5-methyl-1,3,4-thiadiazol-2-yl)-3-methyl-1,3-imidazolin-2-one.

EXAMPLE 13

Preparation of 5-Methoxy-1,3,4-thiadiazol-2-yl Isocyanate Dimer

A saturated solution of phosgene in ethyl acetate (100 ml) is charged into a glass reaction vessel equipped with a mechanical stirrer. A slurry of 5-methoxy-2-amino-1,3,4-thiadiazole (40 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methoxy-1,3,4-thiadiazol-2-yl isocyanate dimer.

EXAMPLE 14

Preparation of the Dimethyl Acetal of 2-[1-Ethyl-3-(5-methoxy-1,3,4-thiadiazol-2-yl)ureido]acetaldehyde A mixture of 5-methoxy-1,3,4-thiadiazol-2-yl isocyanate dimer (0.05 mole), the dimethyl acetal of 2-ethylaminoacetaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 2-[1-ethyl-3-(5-methoxy-1,3,4-thiadiazol-2-yl)ureido]-acetaldehyde.

EXAMPLE 15

Preparation of 1-(5-Methoxy-1,3,4-thiadiazol-2-yl)-3-ethyl-5-hydroxy-1,3-imidazolidin-2-one The dimethyl acetal of 2-[1-ethyl-3-(5-methoxy-1,3,4-thiadiazol-2-yl)ureido]acetaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot and the filtrate is cooled to form a precipitate. The precipitate is recovered by filtration, is dried and is recrystallized to yield the desired product 1-(5-methoxy-1,3,4-thiadiazol-2-yl)-3-ethyl-5-hydroxy-1,3-imidazolidin-2-one.

EXAMPLE 16

Preparation of 1-(5-Methoxy-1,3,4-thiadiazol-2-yl)-3-ethyl-1,3-imidazolin-2-one

A solution of 1-(5-methoxy-1,3,4-thiadiazol-2-yl)-3-ethyl-5-hydroxy-1,3-imidazolidin-2-one (7 grams) in methylene chloride (50 ml) is charged into a glass reaction vessel equipped with a mechanical stirrer and thermometer. The solution is cooled to a temperature of about 10°C and thionyl chloride (3 ml) is added with stirring. After the addition is completed the reaction mixture is allowed to stand at room temperature overnight. After this time the reaction mixture is stripped of methylene chloride by vacuum distillation leaving a solid residue. The residue is then recrystallized to yield the desired product 1-(5-methoxy-1,3,4-thiadiazol-2-yl)-3-ethyl-1,3-imidazolin-2-one.

EXAMPLE 17

Preparation of 5-Methylthio-1,3,4-thiadiazol-2-yl Isocyanate Dimer

A saturated solution of phosgene in ethyl acetate (100 ml) is charged into a glass reaction vessel equipped with a mechanical stirrer. A slurry of 5-methylthio-2-amino-1,3,4-thiadiazole (45 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methylthio-1,3,4-thiadiazol-2-yl isocyanate dimer.

EXAMPLE 18

Preparation of the Dimethyl Acetal of 2-[1-Propyl-3-(5-methylthio-1,3,4-thiadiazol-2-yl)ureido]acetaldehyde A mixture of 5-methylthio-1,3,4-thiadiazol-2-yl isocyanate dimer (0.05 mole), the dimethyl acetal of 2-propylaminoacetaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 2-[1-propyl-3-(5-methylthio-1,3,4-thiadiazol-2-yl)ureido]acetaldehyde.

EXAMPLE 19

Preparation of 1-(5-Methylthio-1,3,4-thiadiazol-2-yl)-3-propyl-5-hydroxy-1,3-imidazolidin-2-one The dimethyl acetal of 2-[1-propyl-3-(5-methylthio-1,3,4-thiadiazol-2-yl)ureido]acetaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot and the filtrate is cooled to form a precipitate. The precipitate is recovered by filtration, is dried and is recrystallized to yield the desired product 1-(5-methylthio-1,3,4-thiadiazol-2-yl)-3-propyl-5-hydroxy-1,3-imidazolidin-2-one.

EXAMPLE 20

Preparation of 1-(5-Methylthio-1,3,4-thiadiazol-2-yl)-3-propyl-1,3-imidazolin-2-one A solution of 1-(5-methylthio-1,3,4-thiadiazol-2-yl)-3-propyl-5-hydroxy-1,3-imidazolidin-2-one (8 grams) in methylene chloride (50 ml) is charged into a glass reaction vessel equipped with a mechanical stirrer and thermometer. The solution is cooled to a temperature of about 10°C and thionyl chloride (3 ml) is added with stirring. After the addition is completed the reaction mixture is allowed to stand at room temperature overnight. After this time the reaction mixture is stripped of methylene chloride by vacuum distillation leaving a solid residue. The residue is then recrystallized to yield the desired product 1-(5-methylthio-1,3,4-thiadiazol-2-yl)-3-propyl-1,3-imidazolin-2-one.

EXAMPLE 21

Preparation of 5-Methylsulfonyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-methylsulfonyl-2-amino-1,3,4-thiadiazole (50 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methylsulfonyl-1,3,4-thiadiazol-2-yl isocyanate dimer.

EXAMPLE 22

Preparation of the Dimethyl Acetal of 2-[1-Methyl-3-(5-methylsulfonyl-1,3,4-thiadiazol-2-yl)ureido]acetaldehyde A mixture of 5-methylsulfonyl-1,3,4-thiadiazol-2-yl isocyanate dimer (0.05 mole), the dimethyl acetal of 2-methyl-aminoacetaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product dimethyl acetal of 2-[1-methyl-3-(5-methylsulfonyl-1,3,4-thiadiazol-2-yl)ureido]acetaldehyde.

EXAMPLE 23

Preparation of 1-(5-Methylsulfonyl-1,3,4-thiadiazol-2-yl)-3-methyl-5-hydroxy-1,3-imidazolidin-2-one The dimethyl acetal of 2-[1-methyl-3-(5-methylsulfonyl-1,3,4-thiadiazol-2-yl)ureido]acetaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot and the filtrate is cooled to form a precipitate. The precipitate is recovered by filtration, is dried and is recrystallized to yield the desired product 1-(5-methylsulfonyl-1,3,4-thiadiazol-2-yl)-3-methyl-5-hydroxy-1,3-imidazolidin-2-one.

EXAMPLE 24

Preparation of 1-(5-Methylsulfonyl-1,3,4-thiadiazol-2-yl)-3-methyl-1,3-imidazolin-2-one A solution of 1-(5-methylsulfonyl-1,3,4-thiadiazol-2-yl)-3-methyl-5-hydroxy-1,3-imidazolidin-2-one (7 grams) in methylene chloride (50 ml) is charged into a glass reaction vessel equipped with a mechanical stirrer and thermometer. The solution is cooled to a temperature of about 10°C and thionyl chloride (3 ml) is added with stirring. After the addition is completed the reaction mixture is allowed to stand at room temperature overnight. After this time the reaction mixture is stripped of methylene chloride by vacuum distillation leaving a solid residue. The residue is then recrystallized to yield the desired product 1-(5-methylsulfonyl-1,3,4-thiadiazol-2-yl)-3-methyl-1,3,-imidazolin-2-one.

EXAMPLE 25

Preparation of 5-Methylsulfinyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-methylsulfinyl-2-amino-1,3,4-thiadiazole (50 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methylsulfinyl-1,3,4-thiadiazol-2-yl isocyanate dimer.

EXAMPLE 26

Preparation of the Dimethyl Acetal of 2-[1-Methyl-3-(5-methylsulfinyl-1,3,4-thiadiazol-2-yl)ureido]acetaldehyde A mixture of 5-methylsulfinyl-1,3,4-thiadiazol-2-yl isocyanate dimer (0.05 mole), the dimethyl acetal of 2-methylaminoacetaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 2-[1-methyl-3-(5-methylsulfinyl-1,3,4-thiadiazol2-yl)ureido]acetaldehyde.

EXAMPLE 27

Preparation of 1-(5-Methylsulfinyl-1,3,4-thiadiazol-2-yl)-3-methyl-5-hydroxy-1,3-imidazolidin-2-one The dimethyl acetal of 2-[1-methyl-3-(5-methylsulfinyl-1,3,4-thiadiazol-2-yl)ureido]acetaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot and the filtrate is cooled to form a precipitate. The precipitate is recovered by filtration, is dried and is recrystallized to yield the desired product 1-(5-methylsulfinyl-1,3,4-thiadiazol-2-yl)-3-methyl-5-hydroxy-1,3-imidazolidin-2-one.

EXAMPLE 28

Preparation of 1-(5-Methylsulfinyl-1,3,4-thiadiazol-2-yl)-3-methyl-1,3-imidazolin-2-one A solution of 1-(5-methylsulfinyl-1,3,4-thiadiazol-2-yl)-3-methyl-5-hydroxy-1,3-imidazolidin-2-one (7 grams) in methylene chloride (50 ml) is charged into a glass reaction vessel equipped with a mechanical stirrer and thermometer. The solution is cooled to a temperature of about 10°C and thionyl chloride (3 ml) is added with stirring. After the addition is completed the reaction mixture is allowed to stand at room temperature overnight. After this time the reaction mixture is stripped of methylene chloride by vacuum distillation leaving a solid residue. The residue is then recrystallized to yield the desired product 1-(5-methylsulfinyl-1,3,4-thiadiazol-2-yl)-3-methyl-1,3-imidazolin-2-one.

EXAMPLE 29

Preparation of 5-Cyclobutyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-cyclobutyl-2-amino-1,3,4-thiadiazole (50 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-cyclobutyl-1,3,4-thiadiazol-2-yl isocyanate dimer.

EXAMPLE 30

Preparation of the Dimethyl Acetal of 2-[1-Propyl-3-(5-cyclobutyl-1,3,4-thiadiazol-2-yl)ureido]acetaldehyde A mixture of 5-cyclobutyl-1,3,4-thiadiazol-2-yl isocyanate dimer (0.05 mole), the dimethyl acetal of 2-propylaminoacetaldehyde (0.1 mole) and benzene (60 ml) are charged into a glass reaction vessel equipped with a mechanical stirrer and reflux condenser. The reaction mixture is heated at reflux for a period of about 15 minutes. After this time the mixture is stripped of benzene under reduced pressure to yield a solid product as the residue. The residue is then recrystallized to yield the desired product the dimethyl acetal of 2-[1-propyl-3-(5cyclobutyl-1,3,4-thiadiazol-2-yl)ureido]acetaldehyde.

EXAMPLE 31

Preparation of 1-(5-Cyclobutyl-1,3,4-thiadiazol-2-yl)-3-propyl-5-hydroxy-1,3-imidazolidin-2-one The dimethyl acetal of 2-[1-propyl-3-(5-cyclobutyl-1,3,4-thiadiazol-2-yl)ureido]acetaldehyde (15 grams), water (400 ml) and hydrochloric acid (4 ml) are charged into a glass reaction vessel equipped with a mechanical stirrer, thermometer and reflux condenser. The reaction mixture is heated at reflux for a period of about 15 minutes. The reaction mixture is then filtered while hot and the filtrate is cooled to form a precipitate. The precipitate is recovered by filtration, is dried and is recrystallized to yield the desired product 1-(5-cyclobutyl-1,3,4-thiadiazol-2-yl)-3-propyl-5-hydroxy-1,3-imidazolidin-2-one.

EXAMPLE 32

Preparation of 1-(5-Cyclobutyl-1,3,4-thiadiazol-2-yl)-3-propyl-1,3-imidazolin-2-one A solution of 1-(5-cyclobutyl-1,3,4-thiadiazol-2-yl)-3-propyl-5-hydroxy-1,3-imidazolidin-2-one (7 grams) in methylene chloride (50 ml) is charged into a glass reaction vessel equipped with a mechanical stirrer and thermometer. The solution is cooled to a temperature of about 10°C and thionyl chloride (3 ml) is added with stirring. After the addition is completed the reaction mixture is allowed to stand at room temperature overnight. After this time the reaction mixture is stripped of methylene chloride by vacuum distillation leaving a solid residue. The residue is then recrystallized to yield the desired product 1-(5-cyclobutyl-1,3,4-thiadiazol-2-yl)-3-propyl-1,3-imidazolin-2-one.

EXAMPLE 33

Preparation of 5-Cycloheptyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-cycloheptyl-2-amino-1,3,4-thiadiazole (50 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-cycloheptyl-1,3,4-thiadiazol-2-yl isocyanate dimer.

EXAMPLE 34

Preparation of the Dimethyl Acetal of 2-[1-Methyl-3-(5-cycloheptyl-1,3,4-thiadiazol-2-yl)ureido]acetaldehyde A mixture of 5-cycloheptyl-1,3,4-thiadiazol-2-yl isocyanate dimer (0.05 mole), the dimethyl acetal of 2-methylaminoacetaldehyde (0.1 mole) and benzene (60 ml) are charged into a glass reaction vessel equipped with a mechanical stirrer and reflux condenser. The reaction mixture is heated at reflux for a period of about 15 minutes. After this time to the mixture is stripped of benzene under reduced pressure yield a solid product as the residue. The residue is then recrystallized to yield the desired product the dimethyl acetal of 2-[1-methyl-3-(5-cycloheptyl-1,3,4-thiadiazol-2-yl)ureido]acetaldehyde.

EXAMPLE 35

Preparation of 1-(5-Cycloheptyl-1,3,4-thiadiazol-2-yl)-3-methyl-5-hydroxy-1,3-imidazolidin-2-one The dimethyl acetal of 2-[1-methyl-3-(5-cycloheptyl1,3,4-thiadiazol-2-yl)ureido]acetaldehyde (15 grams), water (400 ml) and hydrochloric acid (4ml) are charged into a glass reaction vessel equipped with a mechanical stirrer, thermometer and reflux condenser.

The reaction mixture is heated at reflux for a period of about 15 minutes. The reaction mixture is then filtered while hot and the filtrate is cooled to form a precipitate. The precipitate is recovered by filtration, is dried and is recrystallized to yield the desired product 1-(5-cycloheptyl-1,3,4-thiadiazol-2-yl)-3-methyl-5-hydroxy-1,3-imidazolidin-2-one.

EXAMPLE 36

Preparation of 1-(5-Cycloheptyl-1,3,4-thiadiazol-2-yl)-3-methyl-1,3-imidazolin-2-one A solution of 1-(5-cycloheptyl-1,3,4-thiadiazol-2-yl)-3-methyl-5-hydroxy-1,3-imidazolidin-2-one (7 grams) in methylene chloride (50 ml) is charged into a glass reaction vessel equipped with a mechanical stirrer and thermometer. The solution is cooled to a temperature of about 10°C and thionyl chloride (3ml) is added with stirring. After the addition is completed the reaction mixture is allowed to stand at room temperature overnight. After this time the reaction mixture is stripped of methylene chloride by vacuum distillation leaving a solid residue. The residue is then recrystallized to yield the desired product 1-(5-cycloheptyl-1,3,4-thiadiazol-2-yl)-3-methyl-1,3-imidazolin-2-one.

Additional exemplary compounds within the scope of the present invention which can be prepared by the procedures detailed in the foregoing examples are 1-(5-ethyl-1,3,4-thiadiazol-2-yl)-3-methyl-1,3-imidazolin-2-one, 1-(5-butyl-1,3,4-thiadiazol-2-yl)-3-hexyl-1,3-imidazolin-2-one, 1-(5-hexyl-1,3,4-thiadiazol-2-yl)-3-methyl-1,3-imidazolin-2-one, 1(5-ethoxy-1,3,4-thiadiazol-2-yl)-3-methyl-1,3-imidazolin-2-one, 1-(5-propoxy-1,3,4-thiadiazol-2-yl)-3-methyl-1,3-imidazolin-2-one, 1-(5-hexyloxy-1,3,4-thiadiazol-2-yl)-3-methyl-1,3-imidazolin-2-one, 1-(5-ethylthio-1,3,4-thiadiazol-2-yl)-3-methyl-1,3-imidazolin-2-one, 1-(5-butylthio-1,3,4-thiadiazol-2-yl)-3-methyl-1,3-imidazolin-2-one, 1-(5-hexylthio-1,3,4-thiadiazol-2-yl)-3-methyl-1,3-imidazolin-2-one, 1-(5-allyl-1,3,4-thiadiazol-2-yl)-3-methyl-1,3-imidazolin-2-one, 1-(5-but-3-enyl-1,3,4-thiadiazol-2-yl)-3-methyl-1,3-imidazolin-2-one, 1-(5-hex-4-enyl-1,3,4-thiadiazol-2-yl)-3-methyl-1,3-imidazolin-2-one, 1-(5-chloromethyl-1,3,4-thiadiazol-2-yl)-3-methyl-1,3-imidazolin-2-one, 1-(5-$\beta$-chlorethyl-1,3,4-thiadiazol-2-yl)-3-methyl-1,3-imidazolin-2-one, 1-(5-$\gamma$-chloropropyl-1,3,4-thiadiazol-2-yl)-3-methyl-1,3-imidazolin-2-one, 1-(5-trichloromethyl-1,3,4-thiadiazol-2-yl)-3-methyl-1,3-imidazolin-2-one, 1-(5-ethylsulfonyl-1,3,4-thiadiazol-2-yl)-3-methyl-1,3-imidazolin-2-one, 1-(5-propylsulfonyl-1,3,4-thiadiazol-2-yl)-3-methyl-1,3-imidazolin-2-one, 1-(5-hexylsulfonyl-1,3,4-thiadiazol-2-yl)-3-methyl-1,3imidazolin-2-one, 1(5-ethylsulfinyl-1,3,4-thiadiazol-2-yl)-3-methyl-1,3-imidazolin-2-one, 1-(5-butylsulfinyl-1,3,4-thiadiazol-2-yl)-3-methyl-1,3-imidazolin-2-one, 1-(5-hexylsulfinyl-1,3,4-thiadiazol-2-yl)-3-methyl-1,3-imidazolin-2-one, 1-(5-cyclopropyl-1,3,4-thiadiazol-2-yl)-3-methyl-1,3-imidazolin-2-one, 1-(5-cyclopentyl-1,3,4-thiadiazol-2-yl)-3-methyl-1,3-imidazolin-2-one, 1-(5-cyclohexyl-1,3,4-thiadiazol-2-yl)-3-methyl-1,3-imidazolin-2-one, 1-[5-(1-methylcyclohexyl)-1,3,4-thiadiazol-2-yl]-3-methyl-1,3-imidazolin-2-one, 1-[5-(3-ethylcyclohexyl)-1,3,4-thiadiazol-2-yl]-3-methyl-1,3-imidazolin-2-one, 1-[5-(4-butylcyclohexyl)-1,3,4-thiadiazol-2-yl]-3-methyl-1,3-imidazolin-2-one, 1-[5-(4-hexylcyclohexyl)-1,3,4-thiadiazol-2-yl]-3-methyl-1,3-imidazolin-2-one, 1-[5-(2-methylcyclopropyl)-1,3,4-thiadiazol-2-yl]-3-methyl-1,3-imidazolin-2-one, 1-[5-(2-ethylcyclobutyl)-1,3,4-thiadiazol-2-yl]-3-methyl-1,3-imidazolin-2-one, 1[5-(3-methylcyclopentyl)-1,3,4-thiadiazol-2-yl]-3-methyl-1,3-imidazolin-2-one, 1-[5-(4-hexylcycloheptyl)-1,3,4-thiadiazol-2-yl]-3-methyl-1,3-imidazolin-2-one, 1-[5-(3-chlorocyclohexyl)-1,3,4-thiadiazol-2-yl]-3-methyl-1,3-imidazolin-2-one, 1-[5-(4-bromocyclohexyl)-1,3,4-thiadiazol-2-yl]-3-methyl-1,3-imidazolin-2-one, 1-[5-(4-fluorocyclohexyl)-1,3,4-thiadiazol-2-yl]-3-methyl-1,3-imidazolin-2-one, 1-[5-(2-methoxycyclohexyl)-1,3,4-thiadiazol-2-yl]-3-methyl-1,3-imidazolin-2-one, 1-[5-(3-ethoxycyclohexyl)-1,3,4-thiadiazol-2-yl]-3-methyl-1,3-imidazolin-2-one, 1-[5-(4-propoxycyclohexyl)-1,3,4-thiadiazol-2-yl]-3-methyl-1,3-imidazolin-2-one and 1-[5-(4-hexyloxycyclohexyl)-1,3,4-thiadiazol-2-yl]-3-methyl-1,3-imidazolin-2-one.

To effect the method of this invention the plants having storage organs can be treated from the time of their planting to within a late stage of development with an effective amount of an active compound of this invention. Typically the treatment can be carried out at a time period ranging from the time of planting to about two weeks before normal harvesting of the plants.

The amount of the active compound of this invention required to effectively increase the amount of food in the storage organs of plants can vary somewhat depending on such factors as the particular plant involved, the time of application, the weather, crop density and the like. Generally an amount of at least about 0.05 pound per acre and preferably from about 0.1 to about 4 pounds per acre can be used.

For practical use in treating plants with storage organs the compounds of this invention are generally incorporated into compositions or formulations which comprise an inert carrier and an effective amount of such a compound. These compositions enable the active compound to be conveniently applied to the plants in any desired quantity. These compositions can be liquids such as solutions, aerosols or emulsifiable concentrates or they can be solids such as dusts, granules or wettable powders.

The preferred compositions are liquid formulations, particularly emulsifiable concentrates. Emulsifiable concentrates comprise an active compound according to this invention and as the inert carrier, a solvent and an emulsifier. Such emulsifiable concentrates can be extended with water and/or oil to any desired concentration of active compound for application as sprays to the plants.

Typical formulations according to the present invention are illustrated in the following examples wherein the quantities are in parts by weight.

EXAMPLE 37

Preparation of an Emulsifiable Concentrate

The following ingredients are blended thoroughly until a homogeneous liquid concentrate is obtained. This concentrate is mixed with water to give an aqueous dispersion containing the desired concentration of the active ingredients for use as a spray.

| | |
|---|---|
| Product of Example 4 | 25 |
| Sodium lauryl sulfate | 2 |
| Sodium lignin sulfate | 3 |
| Kerosene | 70 |

EXAMPLE 38

Preparation of a Wettable Powder

The following components are mixed intimately in conventional mixing or blending equipment and are then ground to a powder having a particle size of less than about 50 microns. The finished powder is dispersed in water to give the desired concentration of active compound.

| | |
|---|---|
| Product of Example 8 | 50 |
| Fuller's earth | 47 |
| Sodium lauryl sulfate | 2.5 |
| Methyl cellulose | 0.5 |

EXAMPLE 39

Preparation of a Dust

The following ingredients are mixed thoroughly and are then ground to an average particle size of less than about 50 microns to give a dust suitable for application with conventional dusting equipment.

| | |
|---|---|
| Product of Example 4 | 10 |
| Powdered talc | 90 |

The plants with storage organs which may be treated in accordance with the present invention include tuberous species such as potato, sweet potato, yam, cassava, Jerusalem artichoke, Cyperus esculentus and dahlias; species having storage roots such as carrot, turnip, radish, beet including sugar beet; bulb bearing species such as onion, tulip and daffodil; species bearing thickened rhizomes such as iris; and species storing sugar or starch in the stem such as sugar cane, sage and the like.

The treatment of these various plants in accordance with the invention increases the content of plant food in the storage organs. This increase is typically an absolute increase but can be an increase relative to plant weight. Thus, for example, the treatment of potatoes results in an increase in the size and total weight of potatoes per potato plant. Treatment of other plant species of the kind described produces similar increases in the amount of food contained in the storage organs. Often this result is partly due to a modification of the foliar development.

I Claim:

1. A method of increasing the yield of plant food contained in plant storage organs which comprises contacting the plants having storage organs with from about 0.05 to about 4.0 pounds per acre of a compound of the formula

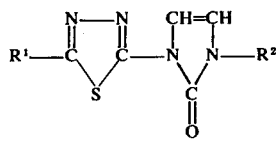

wherein $R^1$ is selected from the group consisting of lower alkyl, lower alkenyl, lower chloroalkyl, trifluoromethyl, lower alkoxy, lower alkylthio, lower alkylsulfonyl, lower alkylsulfinyl and cycloalkyl of from 3 to 7 carbon atoms optionally substituted with from 1 to 2 substituents selected from the group consisting of lower alkyl, lower alkoxy and halogen; and $R^2$ is lower alkyl.

2. The method of claim 1 wherein the compound is 1-(5-trifluoromethyl-1,3,4-thiadiazol-2-yl)-3-methyl-1,3-imidazolin-2-one.

3. The method of claim 1 wherein the compound is 1-(5-t-butyl-1,3,4-thiadiazol-2-yl)-3-methyl-1,3-imidazolin-2-one.

4. The method of claim 1 wherein the compound is 1-(5-methyl-1,3,4-thiadiazol-2-yl)-3-methyl-1,3-imidazolin-2-one.

5. The method of claim 1 wherein the compound is 1-(5-methoxy-1,3,4-thiadiazol-2-yl)-3-ethyl-1,3-imidazolin-2-one.

6. The method of claim 1 wherein the compound is 1-(5-methylthio-1,3,4-thiadiazol-2-yl)-3-propyl-1,3-imidazolin-2-one.

7. The method of claim 1 wherein the plant is a potato plant.

* * * * *